(12) United States Patent
Johansson

(10) Patent No.: US 8,371,696 B2
(45) Date of Patent: Feb. 12, 2013

(54) HIGH PRECISION CONTRAST RATIO DISPLAY FOR VISUAL STIMULUS

(75) Inventor: Göran Anders Johansson, San Francisco, CA (US)

(73) Assignee: Carl Zeiss Meditec, Inc., Dublin, CA (US)

( * ) Notice: Subject to any disclaimer, the term of this patent is extended or adjusted under 35 U.S.C. 154(b) by 0 days.

(21) Appl. No.: 13/405,080

(22) Filed: Feb. 24, 2012

(65) Prior Publication Data

US 2012/0236262 A1 Sep. 20, 2012

Related U.S. Application Data

(62) Division of application No. 12/634,620, filed on Dec. 9, 2009, now Pat. No. 8,132,916.

(60) Provisional application No. 61/122,228, filed on Dec. 12, 2008.

(51) Int. Cl.
*A61B 3/02* (2006.01)
*A61B 3/10* (2006.01)
*A61B 3/00* (2006.01)

(52) U.S. Cl. ......... 351/222; 351/221; 351/205; 351/246

(58) Field of Classification Search ........... 351/200–246
See application file for complete search history.

(56) References Cited

U.S. PATENT DOCUMENTS

| | | | |
|---|---|---|---|
| 4,634,243 A | 1/1987 | Massof et al. |
| 5,202,711 A | 4/1993 | Klingbeil |
| 5,319,398 A | 6/1994 | Weijland |
| 5,323,194 A | 6/1994 | Campbell et al. |
| 5,485,230 A | 1/1996 | Zimmerman |
| 6,121,950 A | 9/2000 | Zavracky et al. |
| 6,388,388 B1 | 5/2002 | Weindorf et al. |
| 6,398,729 B1 | 6/2002 | Levinson |
| 6,705,726 B2 | 3/2004 | Tanassi et al. |
| 6,744,416 B2 | 6/2004 | Mizutani et al. |
| 6,851,809 B1 | 2/2005 | Sachtler |
| 6,891,672 B2 | 5/2005 | Whitehead et al. |
| 7,053,881 B2 | 5/2006 | Itoh |
| 7,101,044 B2 | 9/2006 | Fink |
| 7,113,163 B2 | 9/2006 | Nitta et al. |
| 7,172,297 B2 | 2/2007 | Whitehead et al. |
| 7,193,637 B2 | 3/2007 | Kudo et al. |
| 7,220,006 B2 | 5/2007 | Allen et al. |
| 7,233,310 B2 | 6/2007 | Lazaridis et al. |
| 7,265,743 B2 | 9/2007 | Funamoto et al. |

(Continued)

FOREIGN PATENT DOCUMENTS

| | | |
|---|---|---|
| EP | 1374757 A1 | 1/2004 |
| EP | 1457154 A1 | 9/2004 |

(Continued)

OTHER PUBLICATIONS

International Preliminary Report on Patentability received for U.S. Appl. No. PCT/EP2009/008820, issued on Jun. 14, 2011, 11 pages.
Non Final Office Action received for U.S. Appl. No. 12/634,620, mailed on Jul. 1, 2011, 13 pages.
Notice of Allowance received for U.S. Appl. No. 12/634,620, mailed on Nov. 4, 2011, 17 pages.

(Continued)

*Primary Examiner* — Mohammed Hasan
(74) *Attorney, Agent, or Firm* — Morrison & Foerster LLP

(57) ABSTRACT

Embodiments of the present invention include approaches for controlling light valve devices to improve the range and precision of the contrast ratio and the grayscale levels of a display used for visual field tests. In one embodiment, two or more illumination devices are used to enable the display device to display a wide range of contrast stimuli at precise illumination intensities over a fixed background illumination level. In another embodiment, the gamma curves of the display elements are adjusted to allow greater variations in the brightness of the display.

18 Claims, 7 Drawing Sheets

U.S. PATENT DOCUMENTS

| | | |
|---|---|---|
| 7,333,081 B2 | 2/2008 | Aoki et al. |
| 7,352,352 B2 | 4/2008 | Oh et al. |
| 7,359,008 B2 | 4/2008 | O'Donnell et al. |
| 7,403,332 B2 | 7/2008 | Whitehead et al. |
| 2004/0057013 A1 | 3/2004 | Cappo et al. |
| 2006/0125775 A1 | 6/2006 | Itoh |
| 2006/0132867 A1 | 6/2006 | Sugiyama et al. |
| 2008/0150881 A1 | 6/2008 | Chen et al. |
| 2008/0204481 A1 | 8/2008 | Mostinski |
| 2008/0284979 A1 | 11/2008 | Yee et al. |

FOREIGN PATENT DOCUMENTS

| | | |
|---|---|---|
| WO | 02/00105 A1 | 1/2002 |
| WO | 02/11610 A2 | 2/2002 |
| WO | 2007/026368 A2 | 3/2007 |

OTHER PUBLICATIONS

International Search Report and Written Opinion received for PCT Patent Application No. PCT/EP2009/008820, mailed on Jun. 24, 2010, 14 pages.

Leitgeb R. et al., "Performance of Fourier Domain vs. Time Domain Optical Coherence Tomography", Optics Express, vol. 11, No. 8, Apr. 21, 2003, pp. 889-894.

Orlando et al., "A Programmable Gamma Reference Buffer with Integrated Backlight Control", SID Digest P-49, 2006, pp. 378-381.

Seetzen et al., "High Dynamic Range Display Systems", ACM Transactions on Graphics, Proceedings of Siggraph, 2004, pp. 760-768.

Shiga et al., "Reduction of LCTV Backlight Power and Enhancement of Gray Scale Capability by Using an Adaptive Dimming Technique", SID Digest, 2003, pp. 1364-1367.

Spry et al., "Frequency Doubling Perimetry Using a Liquid Crystal Display", American Journal of Ophthalmology, vol. 131, 2001, pp. 332-338.

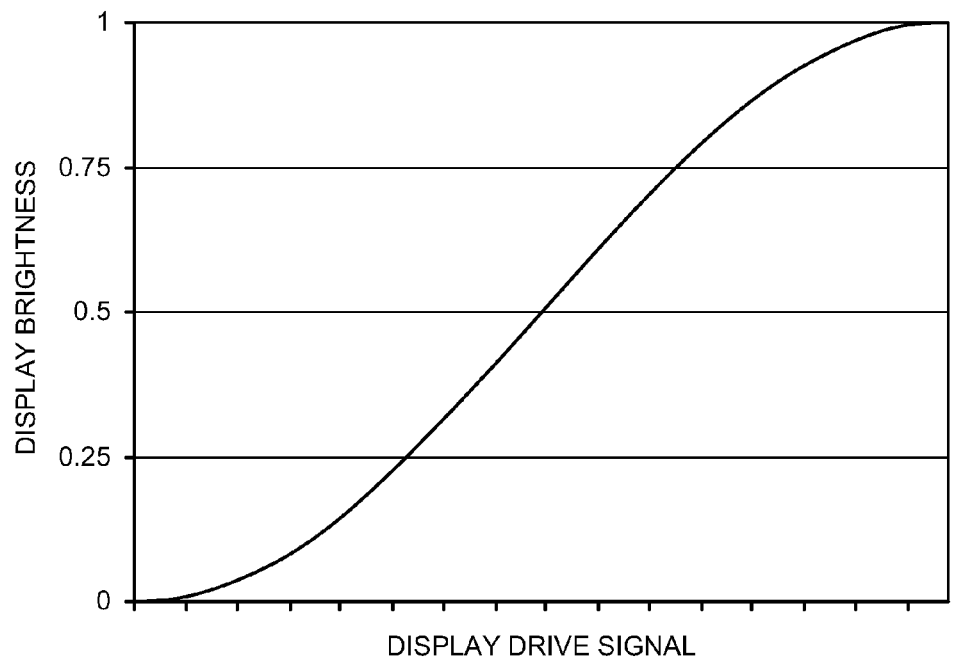
FIG. 7
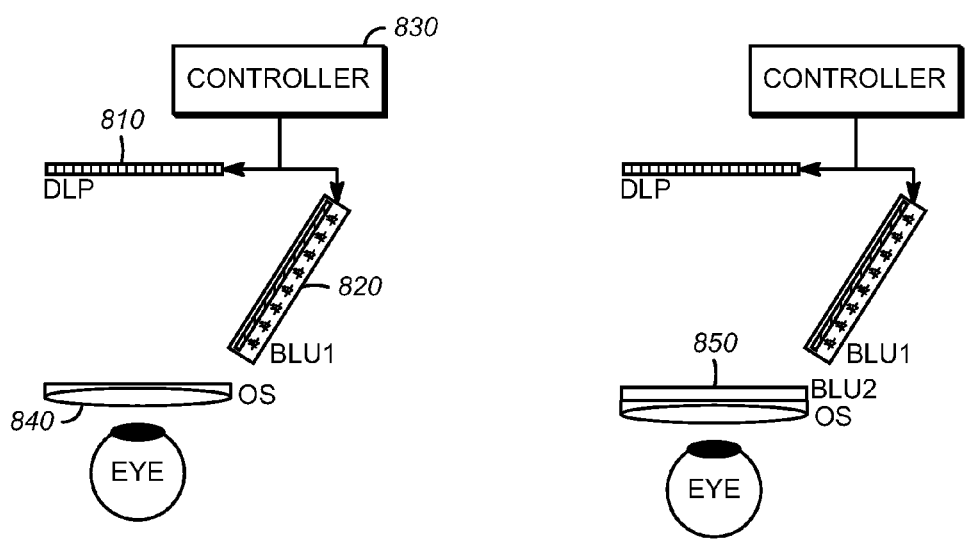
FIG. 8A  FIG. 8B

HIGH PRECISION CONTRAST RATIO DISPLAY FOR VISUAL STIMULUS

PRIORITY

This application is a divisional of U.S. patent application Ser. No. 12/634,620 (now U.S. Pat. No. 8,132,916), filed Dec. 9, 2009, which in turn claims priority to Provisional Application Ser. No. 61/122,228, filed Dec. 12, 2008, the disclosures of which are herein incorporated by reference in their entirety.

TECHNICAL FIELD

One or more embodiments of the present invention relate generally to a method and apparatus for performing a visual field test. In particular, one or more embodiments disclose methods and apparatuses for controlling the displayed images for use in visual field testing. Further, one or more embodiments of the present invention provides the range and precision of the contrast ratio and the grayscale levels required for visual field tests. One or more embodiments disclose methods and apparatuses for controlling a display device and/or backlight units for the purpose of performing visual field testing.

BACKGROUND

A liquid crystal display (LCD) device is a typical light valve apparatus. These devices display images by modifying the transmission of light. They do not emit light by themselves (liquid crystal panel, for example), but rather block portions of light emitted from a backlight source. To cope with this, light valve display devices are generally provided with a light source (backlight, for example) which emits light from the rear side of a passive light modulation part therein to increase visual brightness of a display screen. Accordingly, brightness of the light source can be adjusted in addition to general contrast adjustment, thereby improving visibility of displayed images.

While the DLP™ technology of Texas Instruments (digital light processing) does not block light in the sense that LCD technology does, the DLP technology uses a large numbers of micro-minors to either reflect light or not reflect light for a duration. The result is in many ways similar to allowing a percentage of light through and blocking the remainder. Liquid crystal on silicon (LCoS) is similar to DLP technology in that it reflects light. LCoS differs from DLP in that it uses liquid crystal technology rather than minors to control the amount of light reflecting off of the device. While the invention disclosed herein applies to a variety of backlit display devices, for clarity and conciseness, the description herein will be primarily limited to discussion of LCD devices.

In recent years, consumer products have used LCD display devices in a variety of industrial applications, displaying information such as data, charts, graphs, and images. These displays are increasingly gaining favor for use in medical imaging devices; including visual field examinations (see U.S. Pat. No. 6,705,726). The LCD display is lightweight, compact, exhibits a multiplicity of colors and is high resolution.

For backlit devices, the backlight luminance generally is factory adjusted to provide the desired brightness of the backlight display device. The backlight luminance can later be controlled by modifications of the backlight drive current or voltage. Normally, backlight luminance is varied dependent upon device temperature and environmental lighting, as well as user preference. For user preference modifications, brightness is typically controlled manually using switches, buttons, or keypads, either directly or remotely to adjust the brightness. In some cases, the backlight display luminance is automatically controlled, based on a light sensor or other environmental sensing device to account for environmental conditions. Since device efficiency may be directly linked to device temperature, one such environmental sensor used by some device manufacturers measures temperature.

Passive light valve devices control the transmission of a background radiation light by adjusting the light transmittance, thereby limiting the total contrast available. Common controllers for adjusting the transmittance are generally 6-bit (64 levels) or 8-bit (256 levels). Controllers exceeding 8-bit are uncommon, largely because of cost-benefit constraints, while controllers with fewer than 64 levels generally do not produce enough levels, though is some cases, the 2-bit controller is used when two colors, say black and white, are sufficient. While gamma curves can change the spacing between adjacent levels, the greatest contrast these devices are capable of is set by the highest and lowest transmittance levels. With only limited levels available, it can be impossible to match the specific intensity of a predefined intensity level or levels, even when the number of levels simultaneously displayed is less than the number of levels controllable by the display.

The industry continues its efforts to improve light valve display devices. Embodiments herein enable backlit display devices including, but not limited to, LCD, LCoS, and DLP devices, to increase the number of levels available from the display device, under certain circumstance, such as when used in visual field examinations.

SUMMARY

The present invention is defined by the claims and nothing in this section should be taken as a limitation on those claims. Advantageously, embodiments of the present invention overcome the above-described problems in the art and provide more absolute contrast level steps (contrast ratios) than are available by adjusting the light valve device alone.

In accordance with the present invention, a method and apparatus is provided for controlling the intensity of the backlight illumination as well as the per pixel based light transmission of the light valve device to control total display luminance.

One embodiment of the present invention, a method and apparatus is provided for simultaneously controlling the intensity of the backlight illumination and the per pixel based light transmission of the light valve device to control total display luminance.

In a second embodiment of the present invention, the background illumination and visual stimulus are temporally separated into even and odd frames of the display device, respectively. The display device interleaves the display frames at a rate sufficient for the human eye to integrate the image. The intensity for each frame is controlled by the backlight.

In a third embodiment of the present invention, the background illumination and visual stimulus are temporally separated into even and odd frames of the display device wherein the illumination for each frame is formed by simultaneously controlling the intensity of the backlight illumination and the per pixel based light transmission of the light valve.

In a fourth embodiment of the present invention, the background illumination and visual stimulus are provided separately. The stimulus is provided by a light valve device in combination with a backlight unit and the background illumination is injected in the optical path through a beam splitter or by other means from a separate background light unit.

BRIEF DESCRIPTION OF THE DRAWINGS

FIG. 7 illustrates an intrinsic gamma curve of an LCD device.

FIG. 8a is a schematic illustration of a DLP device and a separately controllable illumination light.

FIG. 8b is a schematic illustration of a DLP device and a separately controllable illumination light and a second independently controlled background light source.

DETAILED DESCRIPTION

Figure 1:
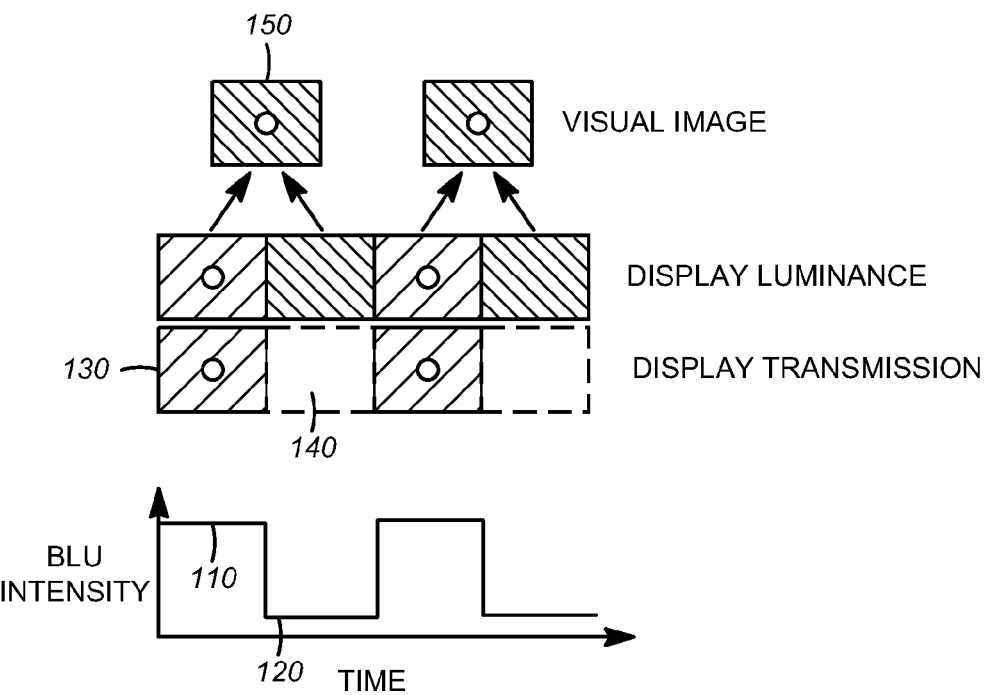
FIG. 1 is a schematic illustration of frame interleaving with light valve switching.

It should be understood that the embodiments, examples and descriptions have been chosen and described in order to illustrate the principles of the invention and its practical applications and not as a definition of the invention. Modifications and variations of the invention will be apparent to those skilled in the art. The scope of the invention is defined by the claims, which includes known equivalents and unforeseeable equivalents at the time of filing of this application.

Prior to this invention it has not been possible to present visual stimuli for a visual field test display with satisfactory luminance levels, dynamic range and grayscale precision using conventional light valve display technologies. Display systems for visual field testing require very high accuracy and control of absolute luminance levels and contrast ratios for visual stimuli. In particular, it can be critical to maintain a background illumination while displaying stimuli that cover a very broad range of intensities. The following description will primarily discuss the LCD display and use the term backlight (or backlit display) to refer to the light being controllably varied by the light valve device, whether such light is behind and passing through the light valve, as in the LCD device, or such light is in front of and reflected off of the light valve, as in DLP or LCoS devices.

A visual field stimulus is target presented within the subject's visual field of view. A stimulus is nominally a target of a predefined shape, size, and intensity presented at a location for a duration. The stimuli is generally presented against a fixed background. The background is everywhere within the subject's visual field except the location of the stimulus. More complicated stimuli may vary in contrast across the target and the target stimulus may vary over time.

The gold standard in visual field analysis has been marketed for some time by the assignee herein under the trademark Humphrey® Field Analyzer (HFA). The HFA projects a light stimulus on an aspherically shaped bowl (see U.S. Pat. No. 5,323,194). One goal of the present invention is to develop a backlit display that can, within the visual field available to it, display a target stimulus with effectively the same absolute luminance as would be perceived in a comparable HFA test. Another goal of the present invention is to develop a backlit display that can, within the visual field available to it, display a frequency doubling illusion target stimulus, such as those displayed by systems marketed the assignee herein under the trademarks Humphrey FDT® perimeter and Humphrey Matrix® perimeter with effectively the same absolute luminosity and contrast as would be perceived in a comparable FDT or Matrix test. For reasons of size, weight and user preference, the preferred backlit display is a flat panel display.

The HFA test image is intuitively quite simple. The HFA presents stimulus targets of various sizes and intensities on a background of fixed, uniform intensity. For example, one HFA stimulus is a white circle of diameter 0.43 degrees presented against a background with a brightness of 31.5 apostilbs for a duration of 200 ms. The stimulus brightness is one of 51 precisely defined intensities and it is presented at a location relative to a fixed position. Nominally, the fixed position is defined relative to a fixation target, on which the subject fixates their gaze.

A small flat display cannot hope to attain the peripheral extent enabled by the HFA bowl. However, a flat panel display can effectively cover a broad angle within the subject's field of view by using a small flat panel device, such as a 6.5 or 8.4 inch device, in combination with a lens system. A display plus lens device can cover all of the diagnostically relevant regions covered by HFA. Furthermore, the numbers of pixels needed to create the various HFA targets on such a flat screen are available in screens with small dot pitch and high resolution, say 1024×768 or better. Smaller displays increase the complexity of the lens system while larger displays increase the overall size of the device when, generally, smaller is better. Regardless, using a high resolution flat panel display plus lens system, one can emulate the HFA stimulus target size, location, and duration within diagnostically relevant locations (such as the central 60 degree cone of vision).

In fact, the display plus lens arrangement resolves one problem experienced by the HFA. By configuring the lens system to place the display in the far field, we allow the subject to focus at infinity removing the necessity for the subject eye to accommodate. This resolves a problem sometimes experienced by older subjects whose natural accommodation is gone. In such cases, the subject requires a lens matching their vision to be inserted for the subject's vision to be tested using the HFA. The display plus fixed lens device removes the need for an operator to configure the equipment for subject accommodation, thus reducing exam set-up time.

The problem remains that the HFA stimulus covers 51 dB in dynamic range in precisely measured retinal sensitivity steps of 1 dB. A typical light valve device cannot match those levels with its 64 or 256 available levels without factory modification of the default display levels. Thus, it is problematic for a light valve device such as an LCD screen, to match all of the stimulus target intensities available to HFA while maintaining a fixed background level. Fortunately, only a limited number of levels are needed. Nominally, there are only two levels necessary for any instance of an HFA test, the background level and the stimulus level. However, some implementations of the HFA stimulus using digital displays may use more than one level in the stimulus, tapering the stimulus intensity near its edge with the background. This problem is resolved herein by means of level shifting, frame interleaving, or multiple backlights, all described below.

Figure 4:
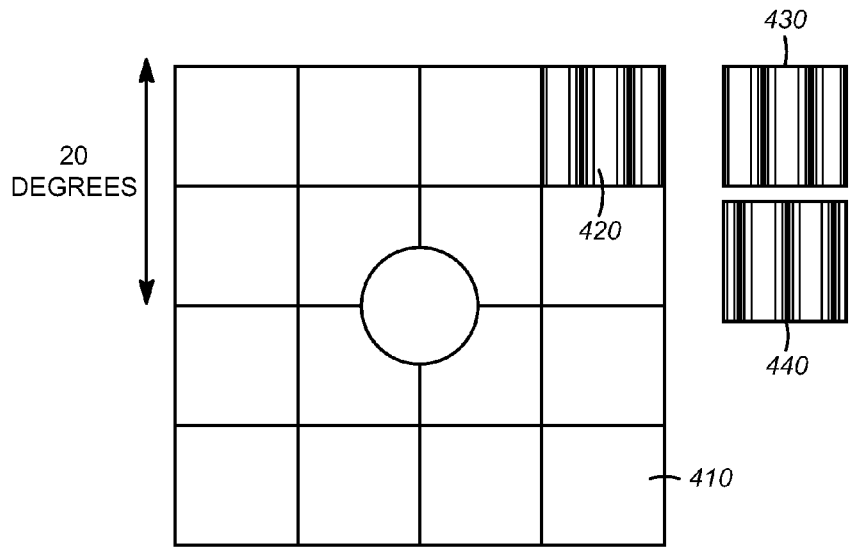
FIG. 4 illustrates a frequency doubling stimulus and a region grid over which it may be applied.

The number of display levels in commercially available light valve display devices is also problematic for displaying a frequency doubling illusion, as in the FDT or Matrix. Conceptually, the frequency doubling illusion might be implemented with as few as two levels, in their contrast extremes, black and white. Nominally the frequency doubling illusion requires a third, intermediary level halfway between these that is the same as the background level. However, typically a much more complicated target is used to present the frequency doubling stimulus. FIG. 4 illustrates the more complex stimulus used for testing the frequency doubling illusion. In FIG. 4, image 430 is one target of the illusion stimulus. Image 430 varies from bright to dark across bands using several illumination levels. Image 440 is the reverse video image of image 430. The examination region is divided into a number of cells such as 410. When testing the subject's vision at a location, the appropriate cell of the grid is chosen, and a target 420 is displayed in that cell. The illusion is created by toggling the two images in the cell from 430 to 440 at a particular frequency. The gold standard frequency doubling illusions stimulus of the FDT and Matrix uses a CRT implementation with 4096 available intensity levels for displaying these contrast changing targets and the target use a number of levels. While level shifting and frame interleaving can reduce the artifacts created in visual field testing using the frequency doubling illusion, the use of multiple backlights allows the production of stimuli diagnostically equivalent to the HFA and Matrix stimuli with fewer artifacts.

Commercially available light modulation display devices generally keep the backlight at essentially a constant intensity. The intensity of the emitted backlight is modulated by the selected transmissivity of the light valve display device to produce the desired luminance of the display. Small variations in the backlight luminance are used to stabilize the variations in monitor brightness due to environmental conditions. The number of available levels of any light valve device are specified by its manufacture. Furthermore, the transfer function for the emitted light luminance given the backlight intensity and light valve level state are dependent on the light valve device, its specifications, and its manufacture. Most display devices based on liquid crystal technology have limited dynamic range ratios between 300 and 800 and a limited number of gray levels, usually either 64 or 256. The actual characteristics for the device depend on the quality of the polarizer, the liquid crystal and the drive electronics.

The contrast ratio exhibited on a display is a ratio based on the luminance at two different regions of a display, usually the maximum and minimum luminance. The specification for a commercial display usually specifies the maximum contrast ratio achievable by the device. The transfer function characterizing the light transmission through the display from the drive voltage may not be smooth, making precise predictions of the absolute luminance levels difficult. Whether the transfer function is smooth or not, a fixed background illumination delineates the levels of luminance available as outputs at each pixel of the display. For grayscale images, the luminance is proportional to the gray level. For the standard configuration of LCD displays used, say in computer monitors, very few luminance levels (grayscale levels) are the same as the levels currently used for visual field testing using HFA.

Embodiments of the invention disclosed herein enable a new generation of perimetry instruments that preserve, or nearly preserve, the current Gold Standard in perimetry display images, while lowering the cost and complexity of the systems. The use of modern backlit display technology improves the flexibility in device design, potentially incorporating new stimuli and tests that are currently not available in present systems. Future implementation of new stimulus types can be achieved at reduced time-to-market and at reduced cost. A video rate system enables the use of high-speed eye tracking for compensation or correction of fixation errors.

Interleave Control of Peak Illumination

In accordance with one aspect of the present invention, a method and apparatus is provided for separate control of the backlight illumination and the per pixel based light transmission of the light valve device. The separately controlled light valve display frame and backlight display frame combine to provide the total display luminance. In one embodiment, the display refreshes interleaved frames at a sufficiently rapid rate so that the combined image does not appear to flicker when viewed by the human eye. In some cases, this rate may be as low as 30-50 Hz, but in this aspect of the invention it is preferred, but not limited to, rates higher than 60 Hz.

FIG. 1 illustrates separate backlight illumination and per pixel light transmission using the frame interleave embodiment. In the first frame 110, the light valve device is used to display target 130. In the second frame 120, the light valve device is uniformly configured for all cells (preferably for full transmittance) and backlight illumination only is displayed 140. The interleaved images are displayed at a high frame rate and the eye perceives the combined image 150.

Figure 2:
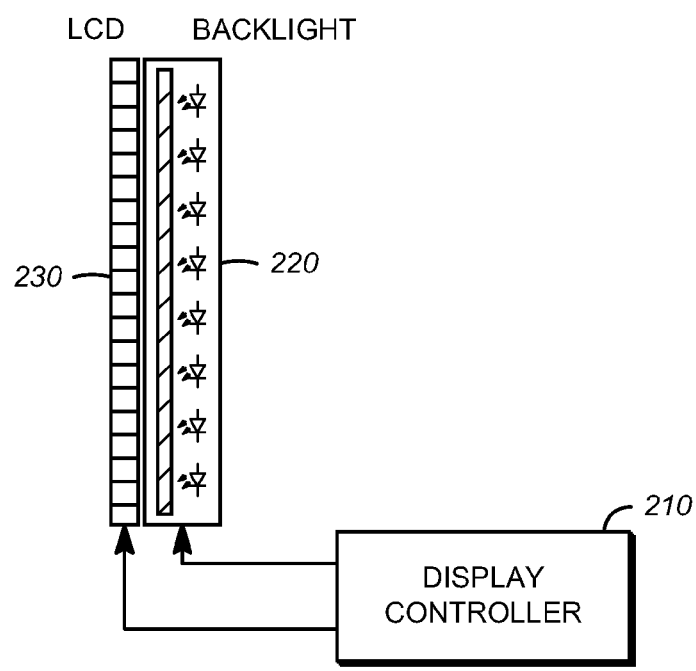
FIG. 2 is a schematic illustration of a light valve device combined with a variable backlight device.

The interleaved frame solution is not achieved without costs. FIG. 2 illustrates one instantiation of this solution using a liquid crystal display (LCD) 230, a backlight 220 and a controller 210 that separately controls both the LCD and the backlight. The embodiment rapidly switches the LCD components from an image display state illustrated in FIG. 1, 130, to an open position, allowing a significant portion of the backlight through, illustrated in FIG. 1, 120. Unlike a standard LCD image, the perceived image achieves its contrast from one frame and perceived luminance from the combination of two frames. The current cost of display components capable of making the fast state transitions necessary to enable the high frame rates required for some visual field test targets are high and likely to limit the general commercialization of this technique until the cost of these components is reduced. Expected refresh rate improvements and cost reduction in this technology will improve commercialization of this embodiment over the next few of years. The technique is currently realizable for systems where cost is not a primary concern and/or frame rate is not an issue or the frame rate issues are resolved.

An extension of this technology interleaves more than 2 frames to reduce flicker or to achieve additional shades or colors. One achieves more perceived luminance levels by changing the backlight intensity and the pixel transparency for each frame of N interleaved frames. For large enough N, virtually any contrast ratio and perceived luminance can be achieved, even with relatively few actual transmission levels at each pixel. In this way, the backlit light valve display device displays a luminance to be perceived by determining a sequence of illumination levels to be displayed and then displaying them at a rate such that a human observer viewing the display will perceive the desired luminance. The frame rate may be as low as 10-15 fps when only two frames need to be combined to perceive the desired luminance. 30 fps is preferred. When more frames must be combined to achieve the desired perceived luminance, higher frame rates are required. Thus, by enabling faster transitions and more complicated control, one can achieve more perceived shades and colors from pixels with limited transmission levels.

Compensation of Slow Response Time for LCD Device

Figure 5A:
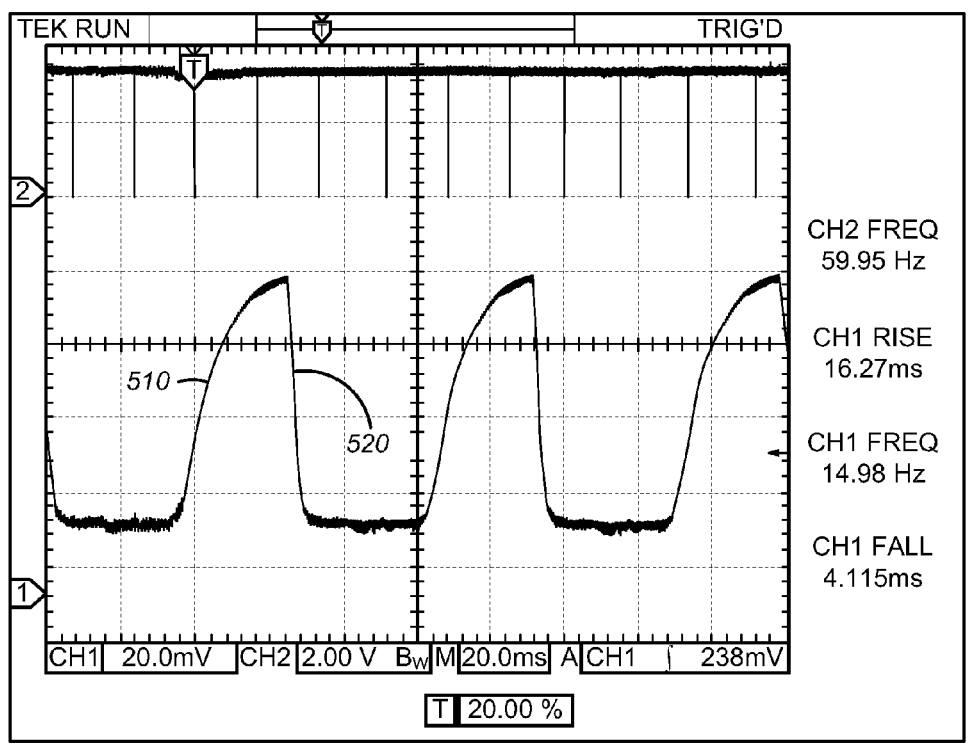
FIGS. 5a and 5b are a plots of the transition times from black to white and white to black for an LCD device.
Figure 5B:
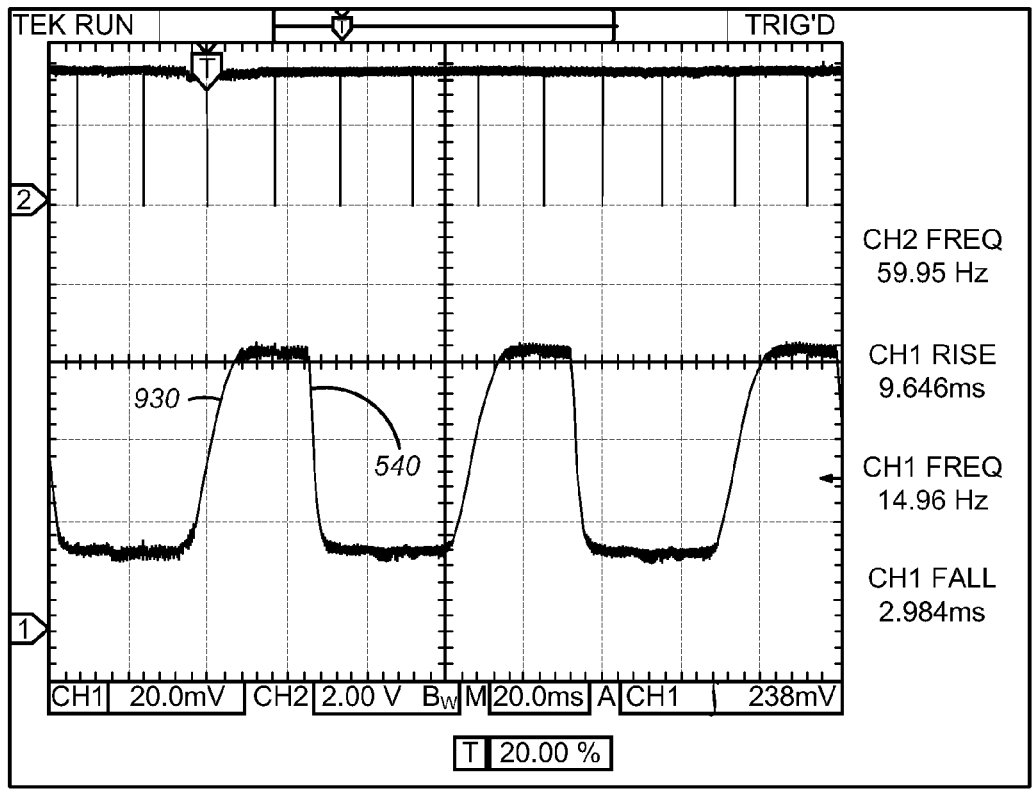

The time required for a light valve device to transition from one state to another is clearly finite. The transition time may depend on the initial and final transmissive states. For example, for a transmissive LCD device, the transition from black to white is generally longer than the transition from white to black. It is advantageous to minimize the transition time for the transition states that require longer times to complete. FIG. 5(a) shows the transition from black to white 510 and the transition from white to black 520. FIG. 5(b) shows the same initial transition from black to white 530, but truncates the transition before white is achieved. The most rapid portion of the transition is the initial portion, as is clearly seen in the rise time of 510. After the initial portion of the transition is complete, the transition is stabilized, either by modifying the state command to the liquid crystal controller or by changing the source light illumination, or both. Either method stabilizes the device so that the more symmetric transitions 530 and 540 are possible. Unfortunately, the peak luminosity available through the device is reduced.

Separate Background and Stimulus Light Sources

Figure 3A:
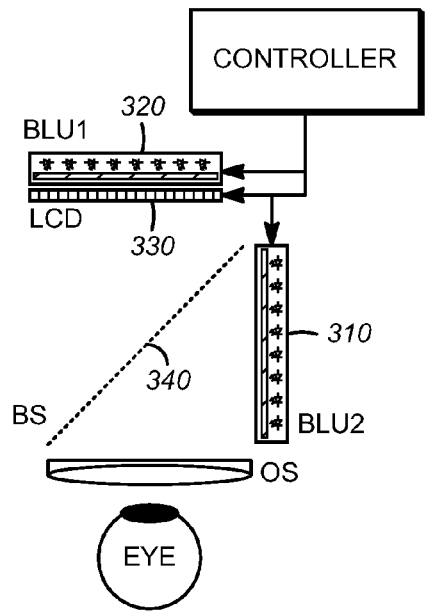
FIG. 3a is a schematic illustration of an LCD combined with a variable LCD stimulus backlight, a second light source (a background light source) independently controlling the background illumination and a beam splitter to combine the two light sources.

In this embodiment, an additional light source (which will be referred to as a background light source) is added to system. Light from the background source is combined with light from the backlight source. The background light source provides a base illumination and the backlight source is used to generate the stimulus. Both the background image and stimulus image are formed, in general, by a combination of light from the background source and the backlight source. The two light source solution provides a system with an arbitrary and independent number of levels (shades or colors) for background and stimulus. FIG. 3a illustrates one implementation of the two light source solution. Here, light source 320 provides the backlight for the light valve 330, in this case a liquid crystal display. The light from the LCD display 330 is combined with the light from source 310 using a beam splitter 340. The background light source 310 may be a physically similar part to the light source 320 and, while not "in back of" the LCD (or even modified by the LCD) it may also be called a backlight. In most configurations the intensity of the stimulus and background is set by both light sources and the shape and size of the stimulus is set by the LCD device and the backlight source. Thus the background and stimulus intensities can be controlled independently and the apparatus for visual field testing is no longer limited by the low contrast ratio and few gray levels available by the LCD device.

The two light source solution does not require the rapid state changes of the display elements required by the single backlight, frame interleave solution discussed above. In some embodiments, the difficulty in the two light source solution rests in the positioning of the additional light source. The solution illustrated in FIG. 3a requires additional space to combine the light sources. Similarly, the arrangement of the light sources in FIG. 3b requires space on either side of the lens 355 as well as geometrically positioning of the backlights 350 and the beam splitter or diffuser 360 used to combine the light from the two light sources and direct the combined light to the lens. Alternatively, the beam splitter or diffuser may be replaced with a wedge, not depicted. The wedge passes light from one source (say the backlight illuminating the LCD) and redirects light from the other source, so that they combine to pass through the lens.

Figure 3B:
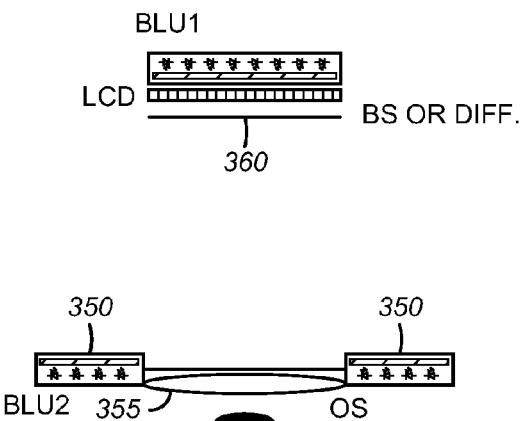
FIG. 3b is a schematic illustration of an LCD combined with a variable LCD stimulus backlight, a second and/or third background light source independently controlling the background illumination and a beam splitter or diffuser to combine the two light sources.

In FIG. 3b, the non-light valve light source 350 (sometimes called background light source or secondary backlight source) is located near the lens 355 to streamline the geometry of the design. The light source 350 may be on one or, as depicted, both sides of the optics system. The beam splitter 360 is positioned to be parallel to the display surface. Alternatively, a diffuser may be used instead of a beam splitter. The component 360 must pass the light out of the LCD while reflecting or dispersing the light from the secondary light source 350.

Whenever a separate background illumination is required, an alternative to using a planar secondary backlight is to place a light source at a conjugate to the pupil. The planar source 310 of FIG. 3a can be replaced with an LED and lens, provided the lens is designed so that the LED is placed at a pupil conjugate. This provides a very uniform background illumination from a simple light source, such as an LED.

Figure 3C:
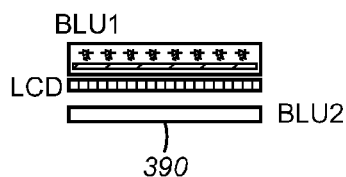
FIG. 3c is a schematic illustration an LCD combined with a variable LCD stimulus backlight and a transparent second light source (background light source) independently controlling the background illumination.
Figure 3D:
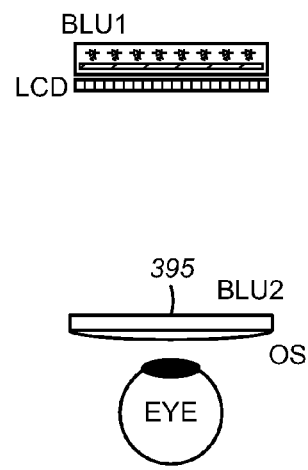
FIG. 3d is a schematic illustration of an LCD combined with a variable LCD stimulus backlight and a transparent second light source (background light source) embedded in or neighboring the lens and independently controlling the background illumination.

In yet another alternative design shown in FIG. 3c, a transparent, or nearly transparent light source 390 can be placed in front of the light valve display. Alternatively, the design shown in FIG. 3d embeds the second light source 395 in the lens. These solutions simplify the geometry significantly. However, they require a high technology light source, such as a phosphorous transparent light source, fluorophore, OLED or quantum dots. Such secondary light sources add their own complications and expense.

We can achieve greater contrast ratios between stimulus and background over short periods by increasing the luminance of the backlight source over its intended level. In doing so, device safety is preserved. While extended periods of increased output create thermal issues and reduce life expectancy, short exposures over periods sufficiently displaced in time can be managed.

Combination Solutions

By combining the methods described above, additional level states can be achieved. For example, if the transfer function of the light valve device is non-linear with respect to the backlight intensity, combining two backlight sources with level shifting increases the number of levels.

We can also increase the number of levels available to the two backlight solution by displaying a sequence luminances at a rate such that the predetermined illumination level is perceived.

Application of Simultaneous Control to Visual Field Testing Devices (Level Shifting)

In accordance with another aspect of the present invention, a method and apparatus is provided for controlling the intensity of a base backlight illumination as well as the per pixel light valve transmission to control the display luminance.

A cathode ray tube display level or color is a function of the energy applied by the electron gun and the fluorescence of the screen. The brightness of a light valve display device is a function of the light input to the valve and the, nominally digital, control, such as the rotation angle of an liquid crystal or the percentage of time the mirror is positioned to reflect light for DLP. The result is the dynamic range and number of brightness levels of the projected image. Since the control for these devices is digital, there are only a finite number of states possible for the light output at a light valve display pixel. For a 6-bit LCD control, there are 64 brightness levels and for an 8-bit LCD controller, there are 256 brightness levels. Generally available controllers for LCD devices are 6-, 8-, and 10-bit controllers.

Figure 6:
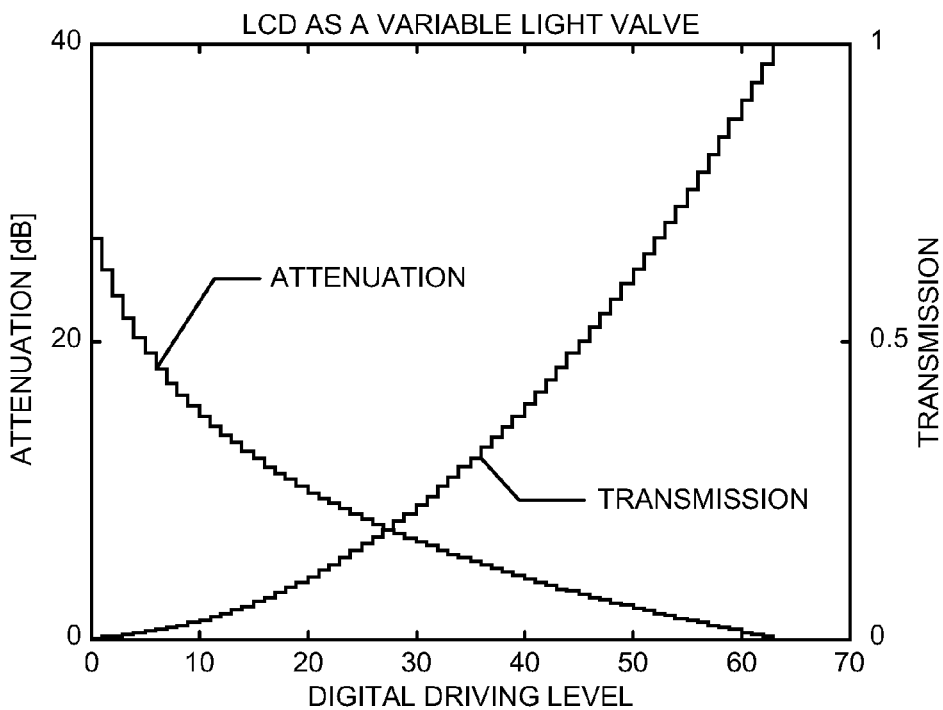
FIG. 6 is a plot of the level steps of an LCD device.

FIG. 6 illustrates the level states of a light valve device. In this illustration, there are 64 states. The change in attenuation or transmission in response to a single step command change in brightness level from the controller is not uniform. As can be seen, the steps between states of low transmission (high attenuation) are much smaller than the steps between states of high transmission (low attenuation).

A priori, for a light valve display using a 6-bit light valve controller, there are only 63 stimulus intensities available, since one shade (or level) is reserved for the background. Even the 8-bit controller only provides 255 stimulus intensities. If these are placed by the manufacturer at the precise levels of the HFA (but different than any known commercial display) they would be sufficient to approximate the HFA. However, if we would like to also display an FDT-like stimulus on the same display and the current CRT implementation of the FDT stimulus and background uses 4096 levels, simply defining 52 of the existing 64 (or 256) levels to be the ones used by the HFA will not allow enough levels to also display the FDT stimulus.

Since the levels on a typical light valve display are not equally spaced, additional levels can be created by using the light valve control and also controlling the backlight intensity. For example, by varying the backlight over 63 different precise intensities so that, one-by-one, each of 63 transmission levels matches the background level, then there are a potential of 63*64/2=2,016 different level of stimulus that can be presented. (That is, there are 63 stimulus levels when the lowest level of transmission is the background, 62 stimulus levels when the background is the second lowest transmission level, etc.) Using an 8-bit light valve controller, this level shifting technique yields a potential of 32,640 different levels and the likelihood of matching the 52 levels required for HFA within the accuracy of the test device is very likely. In this manner, by controlling the backlight intensity and the light valve levels, we can first determine two luminance levels to be displayed and then determine the two light valve levels most closely approximating the spacing between the two luminance levels and finally adjust the backlight intensity so that the two luminance levels are displayed using the two light valve levels. Hence, full control of the backlight makes the 8-bit (and possibly also the 6-bit) controllable light valve displays competitive for HFA visual field analysis.

Level shifting is also useful for some simple implementations of the frequency doubling illusion stimulus similar to the type used by the FDT and Matrix. However, since the frequency doubling illusion implementation in FDT and Matrix uses a stimulus of two targets, each using several levels the two target being video reverse images of one another, plus the background level, judging perceived contrast using the frequency doubling illusion requires many more illumination levels than are required for an HFA visual field analysis. While the non-uniformity in the illumination level spacing of light valve devices is an asset for creating an HFA like stimulus from limited levels, this non-uniformity of the illumination level spacing becomes an obstacle for creating a frequency doubling illusion stimuli. Since the stimulus requires two targets which are reverse video negatives of one another, the non-uniformity of the illumination levels makes the creation of the stimulus pair somewhat complicated. The two stimulus targets are conceptually different for each different illumination level used to display the background, as well as for each different contrast level of the stimulus.

For these reasons, there are significant advantages to displaying the frequency doubling illusion on a light valve display using a two backlight illumination solution. One backlight, the base backlight, controls the lowest level of illumination of the display and illuminates all pixels equally. The other backlight, the light valve backlight, illuminates the light valve and all available levels of the light valve device are used to provide the stimulus intensity profile. The illumination seen on the display is the sum of the base backlight and the light valve backlight. In this way, the contrast of the stimulus target is set by the light valve backlight intensity. The background intensity for the frequency doubling illusion test is a combination of the base backlight illumination and a light valve backlight illumination. The light valve illumination level used for background illumination is the middle level light valve illumination used in the frequency doubling target. The base backlight intensity is then set so that the combination of it and the middle level illumination of the stimulus produce the proper intensity for the background pixels outside the area of the stimulus. By using the two backlight system, the full 64 levels can be used to create the stimulus target and a stimulus of arbitrary contrast (up to the level of control of the light valve backlight intensity) can be displayed on a field of fixed background intensity.

Other Light Valve Devices

For simplicity of description, this specification has, to this point, largely described its embodiments with reference to LCD devices. However, as previously stated, the invention described herein applies to other light valve devices as well. FIG. 8a illustrates a DLP device with a single backlight source. The backlight 820 illuminates the surface mirrors of the DLP device 810. The controller 830 causes the minors of the DLP to reflect the light either toward or away from the viewing window 840. For a fixed set of digital levels of the DLP device, new levels can be achieved by varying the intensity of the backlight 820. FIG. 8b illustrates the addition of a separate background light source 850. The background light source is independent of the DLP and raises the entire background light level by a fixed amount.

Figures 8C, 9:
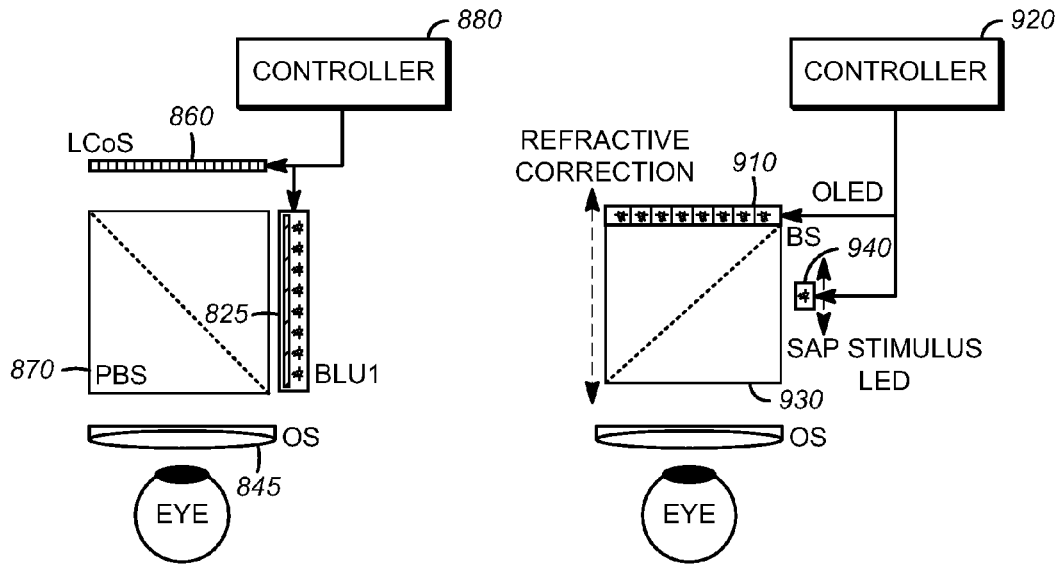
FIG. 8c is a schematic illustration an LCoS device and a separately controllable illumination light.
FIG. 9 is a schematic illustration an OLED display combined with a moveable SAP stimulus source.

FIG. 8c illustrates an LCoS light valve device. Like DLP, LCoS is a reflective technology. Like LCD, LCoS uses polarization properties of liquid crystals fundamentally in its operation. FIG. 8c illustrates LCoS device with a single backlight source. The properly polarized light of backlight 825 reflects off of the polarizing beam splitter 870 to the LCoS device 860. Commands from controller 880 modify the orientation of the liquid crystals in the LCoS device 860, which in turn, modifies the polarization of the light passing through the liquid crystal. This polarized light reflects from a reflecting surface behind the liquid crystal, again passes through the liquid crystal and, with a total change in polarization dependent upon the orientation of the liquid crystal, passes back to PBS 870. PBS 870 transmits some (theoretically between all and none) of the light on through viewing window 845 to reach the eye. An additional background light source (not shown) independent of the LCoS device can be added. For example, a background light source such as 850 of FIG. 8*b* may be added between the PBS and the viewing window 845.

Alternatives Specific to Light Emitting Sources

The LCD and backlight BLU1 of FIGS. 3*a*-3*d* can be replaced by an emissive display using an LED or OLED or other emissive light source. Any light emitting source with sufficient luminance to cover the desired range will do. The deep black levels attainable by the OLEDs is one advantage an OLED has over an LCD, since deep blacks are formed by blockage of light and are impossible to achieve with common commercial LCDs.

Figure 10:
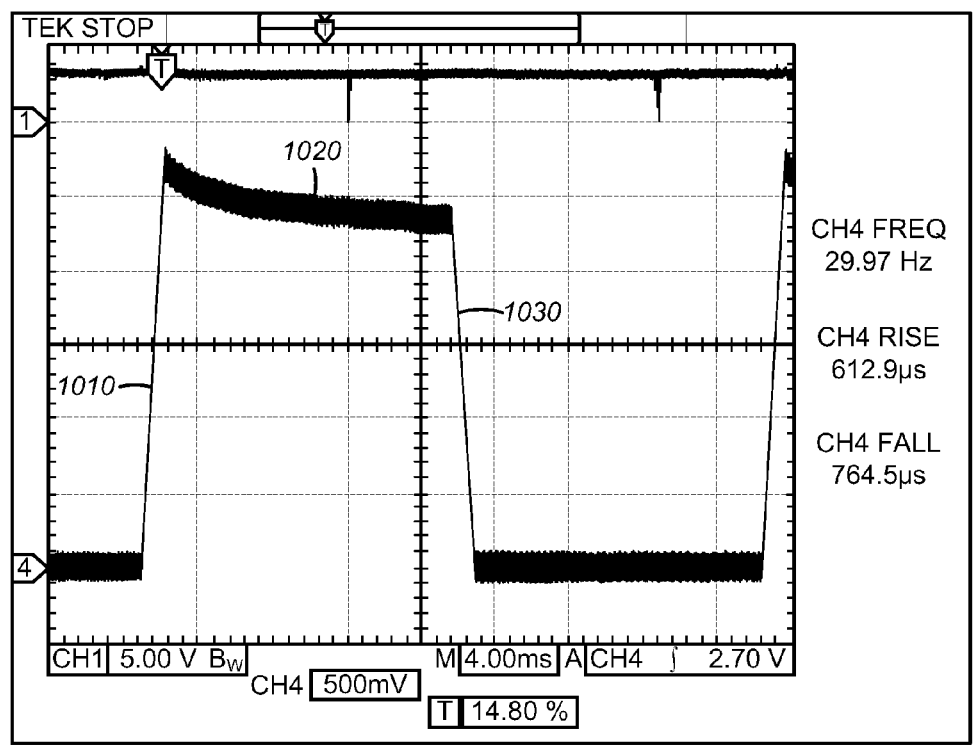
FIG. 10 is a plot of the transition times from black to white and white to black for an OLED device.

Another advantage of OLEDs over LCDs is response time. Many OLED displays are currently specified to have rise and fall times less that 100 μs and the USMP-A34480 (US Micro Products, Inc.) has rise and fall times less than 50 μs. FIG. 10 shows the rapid rise time 1010 from black to white, a slightly decaying white intensity 1020 and a rapid fall time from white to black 1030. While some LCD displays have response times between 1 and 4 ms, typical LCD response times are normally 5-20 ms or longer. Because of the faster response times, display transitions are faster, making it possible to display more rapidly varying visual stimuli.

FIG. 9 illustrates an OLED implementation. In its simplest embodiment, the OLED display would have sufficient intensity and dynamic range to cover all exam types. In that case, beam splitter 930 and stimulus 940 are unnecessary. Controller 920 simply instructs the 2 dimensional OLED display 910 to present the display to be observed. This display could be the stimulus on a background as used in Standard Automated Perimetry (SAP), (either standard white on black or the newer blue on yellow SAP), or a time varying frequency doubling stimulus as used by FDT on a gray background. However, when the maximum intensity of the OLED is insufficient, say for a SAP stimulus, one possible solution would be to reduce the range of the test. However, reducing the range would create customer acceptance issues since the limited range tests would not be comparable to the ophthalmologic standard. A possibly better alternative would be to add target strength to the system by illuminating the stimulus with an additional source, like the one shown in FIG. 9.

The SAP stimulus 940 of FIG. 9 allows the OLED display to be used for a SAP perimetry test, even though the brightest stimulus on the OLED is not sufficient to produce the brightest perimetry stimulus. By adding beam splitter 930 and moveable stimulus 940, the OLED is now used only for the background light level and the fixation target while the SAP stimulus is created by the stimulus source 940, here illustrated by an LED. Since the OLED footprint is small, nominally 2"×2", a small mechanical mount can be used to move the stimulus 940 over the spatial range required.

Other means for scanning the stimulus are: moveable minors placed in front of the stimulus to scan the stimulus onto a collimating lens before the beam splitter; placing the stimulus at the focal point of a parabolic minor and rotating the stimulus to scan the stimulus across the mirror to reflect it to the appropriate location on the eye; using an array of LEDs and illuminating the appropriate one to create the stimulus; etc. Regardless of the mechanism used, the high intensity SAP stimulus can be combined with the OLED background for display to the subject in a manner consistent with FIG. 9. This ability to add a SAP stimulus to an OLED display is of particular importance when producing an instrument for both FDT stimulus and SAP stimulus.

While the OLEDs currently in production do not have sufficient intensity to display a SAP stimulus, they do have the intensity necessary to display an FDT target. (In the future, OLEDs may well provide sufficient intensity to display all necessary SAP stimuli as well.) However, like LCDs, OLEDs have a limited number of colors, because the pixels are addressed by 6- or 8-bit D/A OLED source drivers. So, while there are plenty of colors or shades of gray for a particular FDT target, having only a fixed 64 or 256 shades of gray total is not sufficient to display all of the FDT targets necessary to perform the FDT vision test. As with LCDs, the OLED color table has to be changed for some FDT targets.

Generally, the display can be enhanced by changing the gamma curve. The gamma correction is a (generally programmable) component of the transfer function from the display drive signal to the display brightness. The three primary components of this transfer function are the D/A converter, the gamma correction, and the display element response. The gamma correction is generally a function (often called the gamma function) which, when plotted, is often called the gamma curve. The terms gamma correction, gamma function, and gamma curve are used interchangeably to describe the most readily modifiable component of the transfer function. While every display device material has its own intrinsic physical response to the applied signal, different materials have different responses to the same source signal. Display manufacturers normally have a gamma curve built into their products to modify input signals so that the intrinsic response of their materials to the modified signal will look similar to other displays receiving the same signal. The gamma curve for an OLED is designed so that the OLED display response to a display drive input signal looks similar to the typical response of a CRT, just as the gamma curve for an LCD is designed so that the LCD display response to a display drive input signal looks similar to the typical response of a CRT.

Unlike analog CRTs, digital OLEDs, like LCDs, only display a fixed number of brightness levels. Unfortunately, the levels typically chosen by display manufacturers are not ideal for medical applications. In particular, an ideal FDT display uses pairs of gray levels identically matched above and below the specific level chosen for the background level. This is incompatible with the normal, non-linear gamma function of a typical OLED display.

Of course, the manufacturer can change the gamma function or, if the manufacturer's design permits, provide others with access to change the gamma function. A change in the gamma function changes the transfer function mapping the display drive signal to display brightness. The function of a gamma curve is to provide the information to specify how an initial drive voltage is to be modified to become the actual drive voltage applied to the OLED element. For FDT tests, the preferred gamma curve is symmetric about the background intensity. Since the various FDT stimuli vary the contrast of the stimulus, if a single gamma curve is to be used for all FDT stimuli, the brightness values should be concentrated about the intensity of the background level, as in FIG. 11(*a*). This provides the maximal number of choices for different contrast targets for a single choice of gamma.

However, a single gamma provides only 256 shades of gray for an 8-bit controller (and only 64 shades of gray for a 6-bit controller). If the industry changes to 10-, 12-, or even 16-bit controllers, certainly it will be easier to fit the necessary shades of the various contrast targets into pre-existing gamma curves. However, until then, it will be necessary to make adjustments due to the limited number of shades of gray available. Even if controllers with more control bits become available, these will generally be more expensive and it may well be more cost effective to utilize the present invention than to purchase the more expensive displays.

Figure 11A:
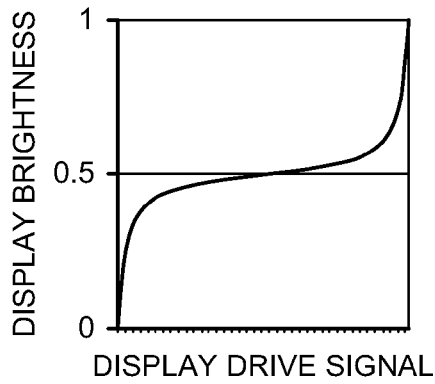
FIG. 11a is a plot of the transfer function from the digital drive signal to display brightness, symmetric about its midpoint, and with a concentration of brightness pixels near that midpoint.
Figure 11B:
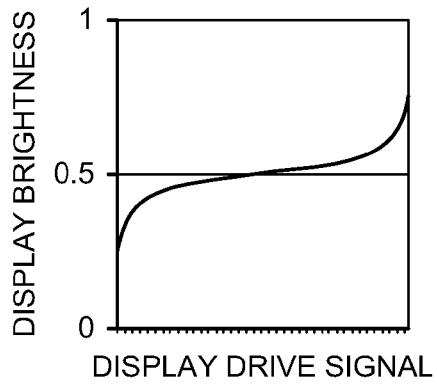
FIG. 11b is a plot of the transfer function from the digital drive signal to display brightness, symmetric about its midpoint, and with limited range.

Certainly complete control of the gamma curve gives you the maximal control of the display. However, the extent of control available is dependent on the manufacturer's specifications. For some chips, there is a pin to control the display brightness range, as shown in FIG. 11(b). Here the range is cut in half while the midpoint (FDT background shade) remains fixed. If the chip only allows control of the maximum brightness (so that the brightness values of FIG. 11(b) would range from 0 to 0.5 instead of from 0.25 to 0.75) then a secondary backlight as discussed previously can be used to boost the overall brightness of the display. This type of control is useful when varying contrast of an FDT stimulus. As is easily seen, the contrast of the stimulus can be varied by changing the display gamma curve, where higher contrast stimuli have a greater range of brightness values in their gamma curve and lower contrast stimuli have a lesser range of brightness values in their gamma curve. This requires sufficient control to change the gamma curve in the time it takes to change from one stimulus to another.

Figure 11C:
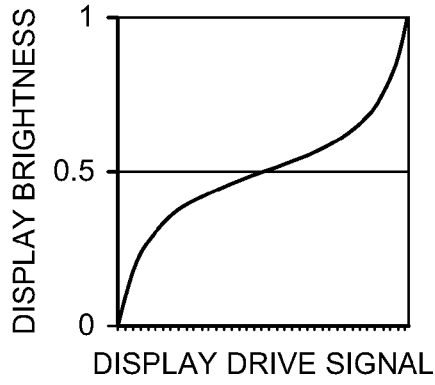
FIG. 11c is a plot of the transfer function from the digital drive signal to display brightness, symmetric about its midpoint, and with a concentration of brightness pixels near that midpoint.

Another control available in some OLED displays allows you to change the slope of the midpoint of the gamma curve. This midpoint should be, for FDT stimuli, the background brightness (which is chosen to be 0.5 for FIG. 11(a)-(c)). FIG. 11(c) illustrates an increased slope of the drive signal to brightness curve when compared to FIG. 11(a). Both curves (FIG. 11(a) and FIG. 11(c)) have the same range, but the greater slope provides access to more brightness shades. Thus, for a high contrast stimulus, the gamma curve is set to produce more bright and dark pixels to choose from and for a low contrast stimulus, the gamma curve is set to produce more shades of gray close to the background display brightness.

Figure 11D:
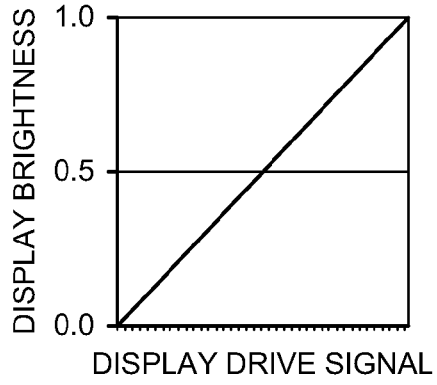
FIG. 11d is a plot of a linear transfer function with slope 1.
Figure 11E:
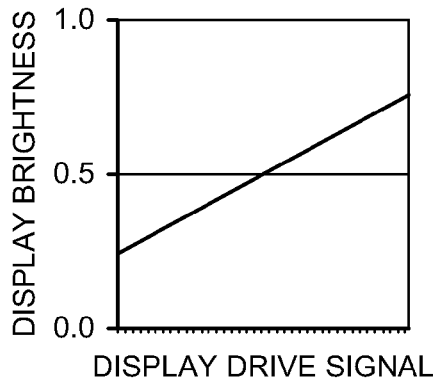
FIG. 11e is a plot of a linear transfer function with slope 0.5.
Figure 11F:
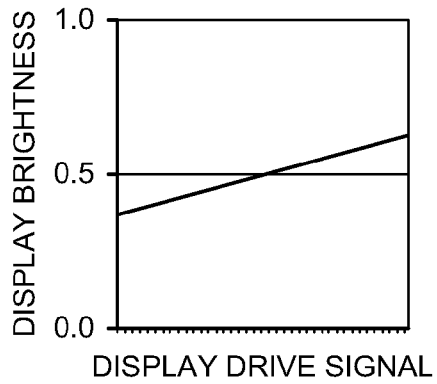
FIG. 11f is a plot of a linear transfer function with slope 0.25.

Control of FDT stimuli is particularly easy when the drive signal to brightness response is linear. FIG. 11(d) illustrates a straight line with slope 1, which allows a maximal contrast stimulus. If you change the gamma curve from that of FIG. 11(d) to one that produces a slope of 0.5 as illustrated in FIG. 11(e), you reduce the contrast of the stimulus displayed without changing the driving signal. Reducing the slope to 0.25, as illustrated in FIG. 11(f), further reduces the contrast of the displayed stimulus without requiring any change to the driving signal. Such a reduction in the range of brightness values provides more shades or colors within the limited range. Thus a low contrast FDT stimulus can display the same number of colors as the high contrast stimulus, even with a limited number of levels, when the slope of the gamma curve is reduced.

Finally, total control of the display can be achieved by modulating the source driver on a pixel-by-pixel basis. This may be accomplished by controlling the gamma curve, if such control can be performed quickly enough, or through and intermediate signal controller. Such control can be complete and continuous or intermittent and partial. Complete and continuous control requires constant monitoring and manipulation of the source driver signal in synchronization with the pixel clock. However, intermittent and partial control can also be accomplished and may be advantageous when a fixed gamma curve is sufficient for all but a few pixels on the display. For example, when the gamma curve is limited to display brightness's over a range of 0.25 to 0.75 as in FIG. 11(b), there is no black. A black fixation target might be useful, covering one or more (but only a select few) pixels. In this case, the source signal can be controlled by setting it to zero regardless of the value out of the D/A for those pixels intended to provide the fixation target.

The fixation target does not need to be black. By making the appropriate choice of the control signal and modulation, any choice of fixation target color can be implemented.

Differential Voltage Drive for Display of Low Contrast Targets

When a wide range of contrast values for stimuli such as sine wave gratings is required for visual field testing, this can be controlled with sufficient accuracy with a "differential" display control. FIG. 7 shows an approximation of the transfer function of an LCD panel. For low-contrast stimuli, it is critical that the display brightness for stimulus pixel be relatively close to the display brightness for the background pixels. In a differential display control, the control signal for each pixel is based on a summation of a background signal and a bi-directional stimulus signal. The stimulus signal may be given a nonlinear transfer function to provide small quantization steps near the zero signal and larger steps at larger signals. A number of nonlinear transfer functions of varying complexity may be designed. One possible implementation of such a transfer function is a cubic, chosen because it is nonlinear, has small quantization steps at low values, and preserves the sign of the input function. The quantization steps are then packed most densely near the background level, as desired. Alternatively, the transfer function may be chosen to directly simulate the steps of existing visual field testing instruments like FDT.

The background signal can remain a fixed value. However, it can also be slowly varying during a test, so long as the variation avoids providing a dynamic stimulus to the patient. The background signal may be calibrated, either during an exam or between exams, to maintain the correct background level and to preserve sufficient precision of displayed stimuli regardless of the stimulus contrast.

Either or both of the background signal and the bi-directional stimulus signal may vary spatially across pixels. For example, to achieve uniform background brightness, the background signal may be calibrated for each pixel to account for pixel-to-pixel variations.

It should be understood that the embodiments, examples and descriptions have been chosen and described in order to illustrate the principles of the invention and its practical applications and not as a definition of the invention. Modifications and variations of the invention will be apparent to those skilled in the art. The scope of the invention is defined by the claims, which includes known equivalents and unforeseeable equivalents at the time of filing of this application.

The following references are hereby incorporated herein by reference.

US Patent Publications

20080204481 Mostinski, Device and Method for Controlling a Backlit Display

20080150881 Chen, et al., Flat panel display and driving method thereof

20060125775 Itoh, Image display device and image display method

US Patent Documents

Display

U.S. Pat. No. 6,388,388 Weindorf, et al., Brightness control system and method for a backlight display device using backlight efficiency U.S. Pat. No. 7,053,881 Itoh, Image display device and image display method U.S. Pat. No. 7,113,163 Nitta, et al., Liquid crystal display apparatus
U.S. Pat. No. 7,172,297 Whitehead, et al., High dynamic range display devices (more like this)
U.S. Pat. No. 7,193,637 Kudo, et al. Display apparatus and driving device for displaying
U.S. Pat. No. 7,220,006 Allen, et al., Method and apparatus for increasing effective contrast ratio and brightness yields for digital light valve image projectors
U.S. Pat. No. 7,265,743 Funamoto, et al., Image display apparatus and image display method
U.S. Pat. No. 7,333,081 Aoki, et al., Image display apparatus, display unit driver and image display method for the same
U.S. Pat. No. 7,352,352 Oh, et al., Liquid crystal display device and controlling method thereof
U.S. Pat. No. 7,359,008 O'Donnell, et al., Dynamic range and contrast enhancement for microdisplay
HDR Technology
U.S. Pat. No. 6,891,672 High dynamic range display device
Visual Field Testing
U.S. Pat. No. 5,323,194 Perimeter with non spherical bowl
U.S. Pat. No. 6,705,726 Instrument for eye examination and method
U.S. Pat. No. 7,101,044 Automated objective characterization of visual field defects in 3D
Other Publications
Leitgeb, R. A., et al. (2003). *Performance of Fourier domain vs. time domain optical coherence tomography. Optics Express* 11(8): 889-894.
Orlando, R. et al., *A Programmable Gamma Reference Buffer with Integrated Backlight Control*, Alta Analog SID 2006 Paper.
Seetzen, Heidrich, Stuerzlinger, Ward, Whitehead, Trentacoste, Ghosh, Vorozcovs: *High Dynamic Range Display Systems*, ACM Transactions on Graphics (Siggraph 2004).

What is claimed is:

1. A method for controlling a backlit light valve display device during a patient vision test comprising:
   determining an illumination level to be perceived;
   determining a background light illumination intensity, wherein the background illumination is not modified by the light valve device;
   determining a light valve backlight illumination intensity, wherein the backlight illumination is modified by the light valve device;
   creating a sequence of frames, each frame composed of light from the background light at a background frame intensity and light valve backlight at a backlight frame intensity; and
   displaying the sequence of frames at a rate which, when viewed by a human, is perceived to be the determined illumination level.

2. A display apparatus comprising:
   a liquid crystal element including an array of pixels with the level of transmission of each element being controllable;
   a source of light located behind the liquid crystal element and directed to illuminate the pixel and with the level of brightness of the light source being controllable; and
   a controller for operating both the liquid crystal element and the light source, said controller receiving information to be displayed, said controller creating a first set of transmission and brightness levels during a first frame and during a second frame, supplying uniform transmission information to all the pixels, said controller alternating between the first frames and the second frame at a rate so that they are perceived by the human eye as a common image.

3. A display as recited in claim 2, wherein the brightness of the source of light is independently adjustable for each of the two frames.

4. A display according to claim 2, wherein the frame rate is at least 10 frames per second.

5. A display according to claim 2, wherein the frame rate is at least 30 frames per second.

6. A method according to claim 2 wherein said uniform transmission corresponds to the maximum level of transmission though the pixels of the liquid crystal element.

7. A display device for use in a visual field test apparatus, said display comprising:
   an array of light valve elements, with the level of transmission of each element being controllable:
   a source of back light located on one side of the array and positioned so that the light generated by the source can be transmitted through the light valve elements and with the level of brightness of the back light being controllable; and
   a controller for controlling the level of transmission of the light valve elements and the level of brightness of the back light source and wherein the controller creates a first set of transmission and brightness levels during a first frame and a second, different set of transmission and brightness levels during a second frame, said controller alternating between the first and second frames at least 10 times per second.

8. A display device as recited in claim 7, wherein the first and second frames are alternated at a rate of at least 30 per second.

9. A display device as recited in claim 7, wherein the set of transmission levels in one of the two sets is arranged for maximum transmission.

10. A display device as recited in claim 7, wherein the controller creates a third set of transmission and brightness levels during a third frame and first, second and third frames are displayed in sequence.

11. A display device as recited in claim 7, further comprising an additional light source, wherein the additional light source is used to expand the available range of transmission and brightness levels.

12. A visual field test apparatus comprising:
   a display having a plurality of pixel elements for generating a background and a plurality stimuli for observation by a patient; and
   a controller for supplying drive signals to the pixel elements, wherein said pixel elements have a level of brightness that varies in response to the level of the drive signal supplied to the elements in accordance with a gamma curve and wherein the slope of the gamma curve near the brightness level corresponding to the background is less than the slope of the gamma curve at the opposed ends thereof.

13. A visual field test apparatus as recited in claim 12, wherein the stimuli are frequency doubling technology (FDT) stimuli.

14. A visual field test apparatus as recited in claim 12, wherein the stimuli are standard automated perimetry (SAP) stimuli.

15. A visual field test apparatus as recited in claim 12, wherein the plurality of pixel elements are light emitting elements.

16. A visual field test apparatus as recited in claim 15, wherein the light emitting elements are light-emitting diodes (LEDs).

17. A visual field test apparatus as recited in claim 15, wherein the light emitting elements are organic light-emitting diodes (OLEDs).

18. A visual field test apparatus as recited in claim 15, wherein the gamma curve is symmetric about the brightness level corresponding to the background.

* * * * *

UNITED STATES PATENT AND TRADEMARK OFFICE
CERTIFICATE OF CORRECTION

| | | |
|---|---|---|
| PATENT NO. | : 8,371,696 B2 | Page 1 of 1 |
| APPLICATION NO. | : 13/405080 | |
| DATED | : February 12, 2013 | |
| INVENTOR(S) | : Goran Anders Johansson | |

It is certified that error appears in the above-identified patent and that said Letters Patent is hereby corrected as shown below:

On Title page 2, item 56 under "OTHER PUBLICATIONS", in column 2, line 11, delete "LCTV" and insert -- LCD TV --, therefor.

In column 11, line 23, delete "that" and insert -- than --, therefor.

In column 15, line 60, in claim 2, delete "pixel" and insert -- pixels --, therefor.

In column 16, line 1, in claim 2, delete "frames" and insert -- frame --, therefor.

In column 16, line 11, in claim 6, delete "method" and insert -- display --, therefor.

In column 17, line 6, in claim 17, delete "(OLED s)." and insert -- (OLEDs). --, therefor.

In column 18, line 1, in claim 18, delete "claim 15," and insert -- claim 12, --, therefor.

Signed and Sealed this
Ninth Day of April, 2013

Teresa Stanek Rea
*Acting Director of the United States Patent and Trademark Office*